US00PP23665P2

(12) United States Plant Patent
Rawson

(10) Patent No.: US PP23,665 P2
(45) Date of Patent: Jun. 11, 2013

(54) ***HOSTA* PLANT NAMED 'RHINO HIDE'**

(50) Latin Name: ***Hosta hybrida* (Tratt.)**
Varietal Denomination: Rhino Hide

(76) Inventor: Donald A Rawson, Comstock Park, MI (US)

( * ) Notice: Subject to any disclaimer, the term of this patent is extended or adjusted under 35 U.S.C. 154(b) by 0 days.

(21) Appl. No.: 12/803,653

(22) Filed: Jul. 1, 2010

(51) Int. Cl.
*A01H 5/00* (2006.01)

(52) U.S. Cl.
USPC ..... Plt./353

(58) Field of Classification Search ..... Plt./353
See application file for complete search history.

*Primary Examiner* — Annette Para

(57) ABSTRACT

A new and distinct *Hosta* plant named 'Rhino Hide' characterized by nearly rounded leaves having thick substance, and variegation of wide bluish-green margins and golden chartreuse centers. The new plant has demonstrated slug resistance beyond any other tested cultivars and also avoidance of late spring frosts. It is able to tolerate full-sun conditions without burning of leaves. *Hosta* 'Rhino Hide' produces early season near white flowers above the foliage and is suitable for garden landscape, potted culture, or cut flower and foliage arrangements.

1 Drawing Sheet

Botanical classification: *Hosta hybrida* (Tratt.).
Variety denomination: 'Rhino Hide'.

BACKGROUND AND ORIGIN OF THE PLANT

The present invention relates to the new and distinct *hosta* plant, *Hosta* 'Rhino Hide' discovered by Donald A. Rawson in the summer of 2000 at a garden in Comstock Park, Mich. The new plant was discovered as an un-induced whole plant growing in a bed of *Hosta* 'Love Pat' (not patented). It is not known whether the new plant is a sport of 'Love Pat' or a random seedling. *Hosta* 'Love Pat' is reported to be a seedling between *Hosta* 'Blue Velvet' (not patented) as the pod or female parent and *Hosta* 'Blue Vision' (not patented) as the pollen or male patent. *Hosta* 'Rhino Hide' was first asexually propagated by division at the garden in Comstock Park, Mich. in 2004 and all resulting plants have retained all the same traits as the original plant. The plant has also been asexually propagated by division by the inventor and also asexually by tissue culture at a nursery in Zeeland, Mich., with the resultant plants in both cases of this asexual propagation maintaining all the same traits of the original plant. The plant is stable and reproduces true to type in successive generations of asexual reproduction.

The most similar known *hosta* cultivars are: *Hosta* 'Tokudama Aureonebulosa' (not patented), *Hosta* 'Great Expectations' (not patented), *Hosta* 'Love Pat' (not patented) and *Hosta* 'Love Burst' (not patented). *Hosta* 'Tokudama Aureonebulosa' and *Hosta* 'Love Burst' (not patented) are the most similar in color. *Hosta* 'Love Burst' is a viridescent sport of 'Love Pat' with a lighter center variegation that becomes bluish-green by mid season, and the variegation is not noticeable for the remainder of the season. *Hosta* 'Great Expectations' has much more white to creamy-white in the center leaf portion rather than the greenish-gold coloration of the center of the leaf of 'Rhino Hide'. The most unique trait setting *Hosta* 'Rhino Hide' apart from all other known *hostas* is the thickness of the mature leaf and tepal tissue as measured by a micrometer to the nearest 0.005 mm. 'Rhino Hide' leaf thickness measures 0.430 mm in the space between the leaf veins while other cultivars, including those thicker leaf tetraploid forms are between 0.165 mm and 0.380 mm. Tepal thickness of 'Rhino Hide' is about 0.080 mm whereas tepal thickness of all other *hostas* measured ranged from 0.040 mm to 0.065 mm.

TABLE OF COMPARATIVE LEAF THICKNESS

| HOSTA CULTIVAR | MEAN |
|---|---|
| 'Blue Ivory' | 0.305 mm |
| U.S. Plant Pat. No. 19,623 | |
| 'Grand Marquee' | 0.395 mm |
| U.S. Plant Pat. No. 15,961 | |
| 'Great Expectations' (not patented) | 0.255 mm |
| 'Liberty' | 0.320 mm |
| U.S. Plant Pat. No. 12,531 | |
| 'Love Pat' (not patented) | 0.230 mm |
| 'Rainbow's End' | 0.240 mm |
| U.S. Plant Pat. No. 17,251 | |
| 'Rhino Hide' | 0.445 mm |
| 'Sum and Substance' (not patented) | 0.305 mm |
| 'Thunderbolt' | 0.320 mm |
| U.S. Plant Pat. No. 14,232 | |
| 'Titanic' | 0.305 mm |
| U.S. Plant Pat. No. 12,402 | |
| 'Tokudama Aureonebulosa' (not patented) | 0.305 mm |
| 'Touch of Class' | 0.370 mm |
| U.S. Plant Pat. No. 13,080 | |

SUMMARY OF THE PLANT

*Hosta* 'Rhino Hide' differs from all other *hostas* known to the applicant, in combination of the following traits.

1. Cupped rugose foliage with very wide bluish-green margins and chartreuse to light green or yellow leaf center.
2. Thick-substanced leaves resistant to slugs, tolerant of full sun and late emerging in the spring to avoid damage from late spring frosts.
3. Near white flowers of thick heavy-substance petals in June on compact scapes just above foliage.
4. Large, stout and stiff petioles.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
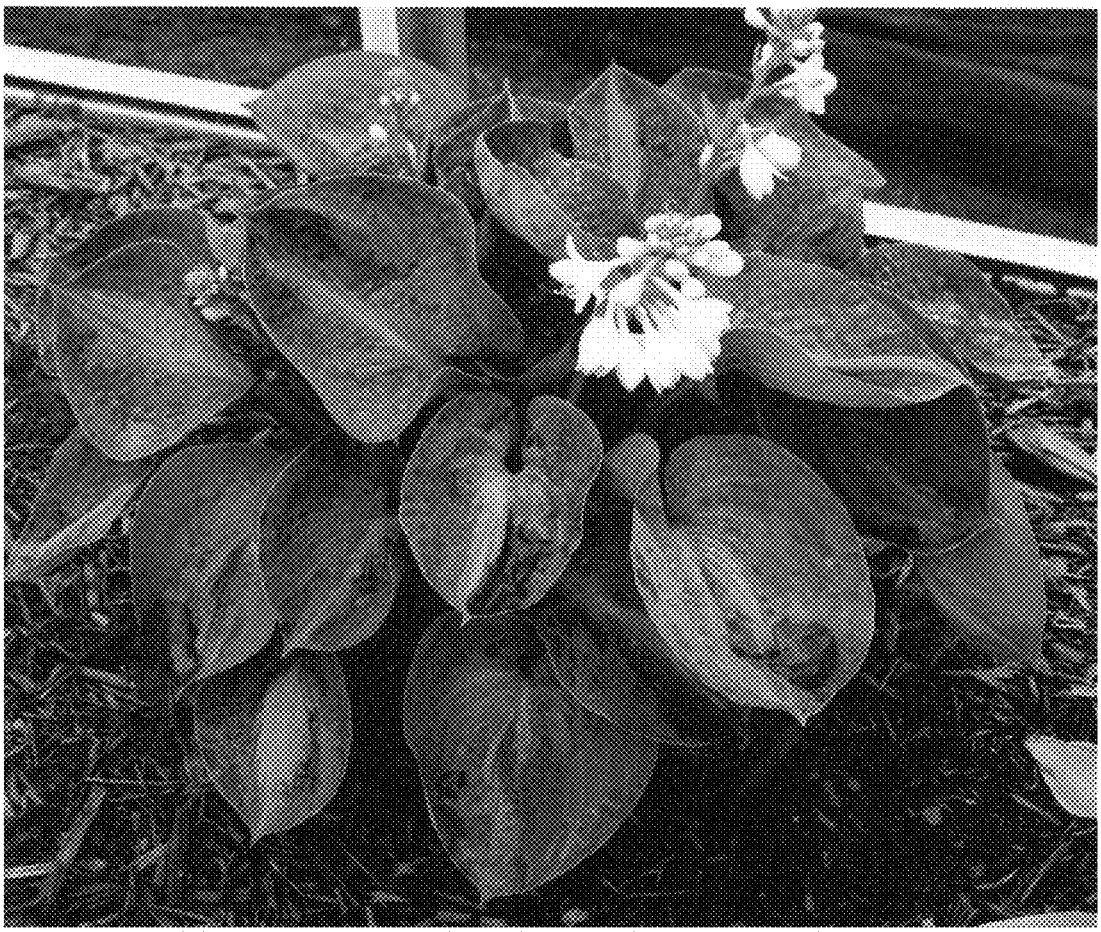
FIG. 1 shows the new plant in the landscape.
Figure 2:
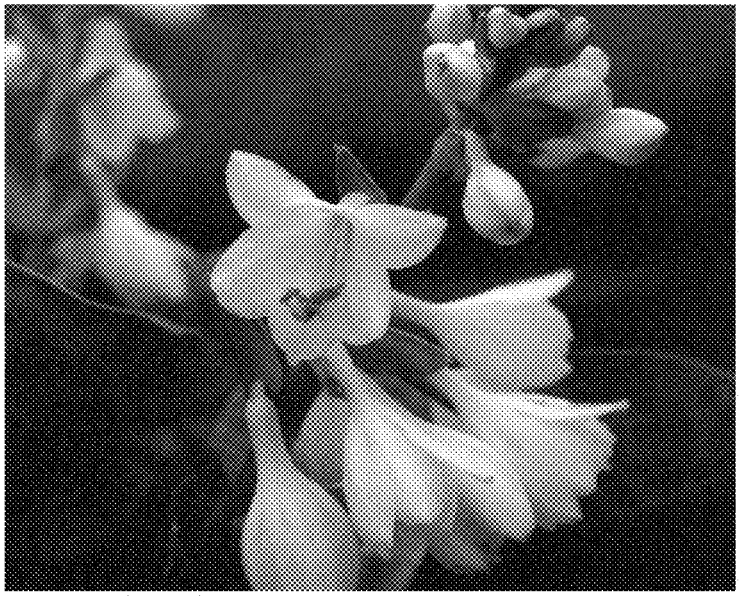
FIG. 2 shows a close-up of the flowers, buds and bracts on the scape of the new plant.

The following descriptions and color references are based on the 2001 edition of The Royal Horticultural Society Colour Chart except where common dictionary terms are used. The new plant, *Hosta* 'Rhino Hide', has not been observed under all possible environments. The phenotype may vary slightly with different environmental conditions, such as temperature, light, fertility, moisture and maturity levels, but without any change in the genotype. The following observations and size descriptions are of a seven-year old plant in a garden in Comstock Park, Mich. with partial shade and supplemental water and fertilizer.

Botanical classification: *Hosta hybrida* (Tratt.)

Parentage: Unknown;

Propagation: Garden division and sterile plant tissue culture;

Time to initiate roots from tissue culture: About three weeks;

Growth rate: Slow to moderate;

Crop time: About 15 to 20 weeks to finish during the summer in a one-liter container from rooted tissue culture plantlet;

Rooting habit: Fleshy, lightly branching, with roots up to 60 cm long;

Plant shape and habit: Hardy herbaceous perennial with basal rosette of leaves producing symmetrical mound of stiff mostly-upright petioles and nearly rounded leaf blades, from rhizomes;

Plant size: Foliage height about 75 cm tall from soil line to the top of the leaves and about 50 cm wide at widest point.

Foliage description: Rounded, very thick substance (adaxial to abaxial dimension), apex obtuse to rounded, base auriculate with lobes frequently overlapping;

Leaf blades: Simple, convex to 8 cm deep, rugose, glabrous and heavily glaucous on both surfaces; entire margin; 20 cm long, 20 cm wide; bi-laterally symmetrical; variegation pattern variable with the margin occupying between about 50% to 75% of the leaf and the leaf center being about 5 to 7.5 cm wide with feathering streaks in between margin and center;

Leaf blade color: Early spring adaxial margin color nearest RHS 137C with a glaucous bloom overlay between RHS 118C and RHS 119C, early spring abaxial margin with glaucous bloom between RHS 122C and RHS 122D; early spring center adaxial side between RHS N144C and RHS 144B with abaxial side the same as adaxial; after flowering adaxial margin more bluish than RHS N138B and more green than RHS 119C, center adaxial side nearest RHS N144A; margin abaxial side more green than RHS 122C and abaxial center lighter yellow than RHS 151A;

Petiole: Concave, stiff and inflexible, about 2.0 cm wide at base and 30 cm long;

Petiole color: Nearest RHS N138C on both adaxial and abaxial margins and more yellow than RHS 138D of both surfaces in the leaf center;

Veins: Parallel, ridged on abaxial side, rejoining or fusing in outer leaf portion, 15 to 17 pair, Veins color: Abaxial veins between RHS 145 C and RHS 145 B with glaucous coating in margin and nearest RHS 154 C in the center and nearest RHS 122 D on the adaxial side;

Flower description:

Buds one day prior to opening: Globose apex with base narrowing to claw; white with a greenish tinting of much lighter than RHS 145D at base and whiter than any RHS color in the distal ⅓ part of claw nearly all the way to apex with the apical 2 to 3 mm nearest RHS N144C; veins on tepals impressed, occasionally with light lavender lighter than RHS 85D;

Flowers: Funnelform; 25 to 30 per scape; 2.5 to 3.0 cm wide and 4.0 to 4.5 cm long, (distal flowers being smaller), persists for a normal period, usually one day on plant or as cut flower; scapes remain effective from mid-June into mid-July with peak in late June; no detectable fragrance:

Bracts: Each flower subtended by a single bract distally decreasing in size with largest about 3.0 cm long and 2.0 cm wide; glaucous and glabrous both surfaces, margin entire, sessile, apex acute; concaved supporting flower bud; nearest RHS 138C in abaxial center and nearest RHS 138A with purplish tinting of nearest RHS N187B on the abaxial margin; adaxial side is nearest RHS 138C on margin and center;

Tepal: Two sets of three, fused at base; clavate with obtuse to cuspidate apex; glabrous, entire; inner set have convex ridge about 3 mm wide in blade portion; approximately 4.0 cm long and 1.5 cm wide and 0.81 mm thick; coloring of both sets identical; predominately white, lighter than any RHS color on the outside; inside whiter than any RHS color with occasional vein colors of lighter than RHS 85D;

Gynoecium: Style: single, 3.3 to 3.5 cm long, white, 1 mm diameter, curled upward at distal end;

*Stigma.*—Globose, about 1 mm in diameter, whiter than any RHS color;

Androecium: Filaments: six, white, less than 1 mm in diameter and 3.0 cm long;

*Anthers.*—2 to 3 mm long, 1 mm wide, dehiscent longitudinally, nearest RHS 163 A;

*Pollen.*—Elliptical, less than 0.1 mm long, nearest RHS 17 A;

Peduncle: One per mature division; glaucous; leaning at 60 degrees from horizontal to erect 45 to 52 cm tall, and up to 9 mm in diameter at base, nearest RHS 138 C;

Pedicel: Approximately 6 mm long, 2 mm wide; RHS 138 C;

Fruit: Tri-loculicidal capsule, about 2.5 to 3.0 cm long and 7 mm diameter; nearest RHS 165C;

Seed: Flattened single-winged nutlet with swollen embryo at one end; about 5 mm long, 2 mm wide and 1 mm thick at embryo; nearest RHS 202A;

Disease resistance: The new plant has shown superior resistance to slugs in garden test comparisons beyond all other *hostas* known to the inventor as well as avoidance of late spring frosts. The plant grows best and shows best coloration with plenty of moisture, adequate drainage and light shade, but is able to tolerate some drought when mature and direct sun without leaf burn when provided sufficient water. Hardiness at least from USDA zone 3 through 9, and other disease resistance is typical of that of other *hostas*.

I claim

1. A new and distinct cultivar of ornamental *Hosta* plant named 'Rhino Hide' as herein described and illustrated, with thick-substance variegated leaves having wide bluish-green margins, golden-chartreuse leaf centers and near white flowers resistant to slugs and full sun conditions and suitable as a potted plant, for the garden, and for cut flower arrangements.

* * * * *